United States Patent [19]

Soloway

[11] 4,423,637

[45] Jan. 3, 1984

[54] ULTRASONIC TESTING INSTRUMENT AND METHOD

[76] Inventor: Mahlon R. Soloway, 202 Sunrise Hill Rd., Norwalk, Conn. 06851

[21] Appl. No.: 217,778

[22] Filed: Dec. 18, 1980

[51] Int. Cl.³ .......................................... G01N 29/04
[52] U.S. Cl. ..................................... 73/642; 310/335; 310/336
[58] Field of Search .................. 73/642, 644; 310/334, 310/335, 336

[56] References Cited

U.S. PATENT DOCUMENTS 3,472,065 10/1969 Maxwell ................................. 73/642
3,550,438 12/1970 Kapluszak ........................ 310/336 X
3,832,889 9/1974 Bauer ..................................... 73/642
3,934,460 1/1976 Sherwin et al. ................. 310/336 X
3,968,459 7/1976 Jacobson .......................... 310/335 X

FOREIGN PATENT DOCUMENTS 52-64920 5/1977 Japan ..................................... 73/642
211859 9/1968 U.S.S.R. .............................. 310/335

Primary Examiner—Charles A. Ruehl
Attorney, Agent, or Firm—DeLio and Libert

[57] ABSTRACT

An ultrasonic testing instrument and a method of non-destructive and non-invasive testing. The instrument and method employ a high intensity collimated ultrasonic beam. The collimated beam is achieved by means of acoustical lenses and/or reflectors.

28 Claims, 14 Drawing Figures

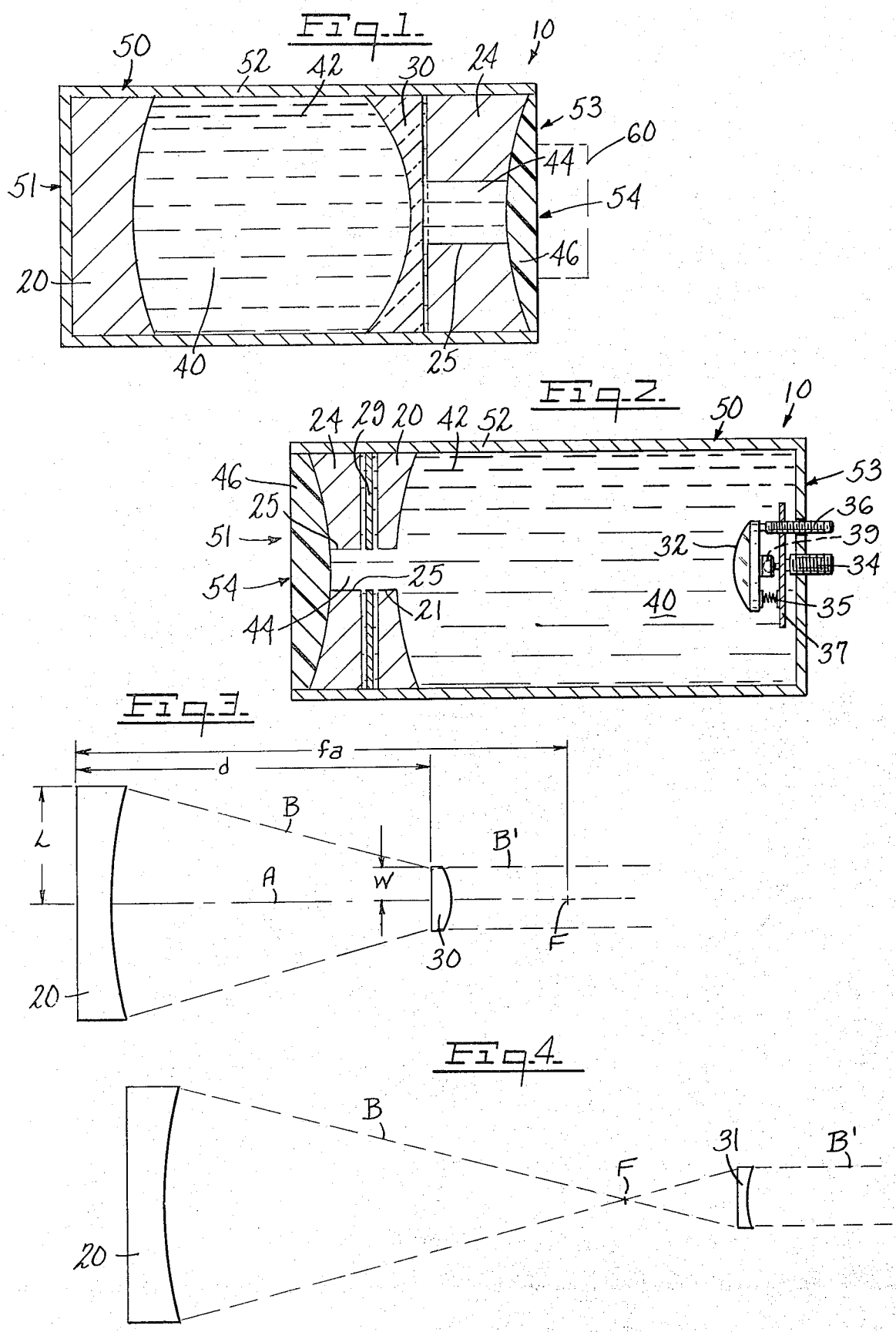

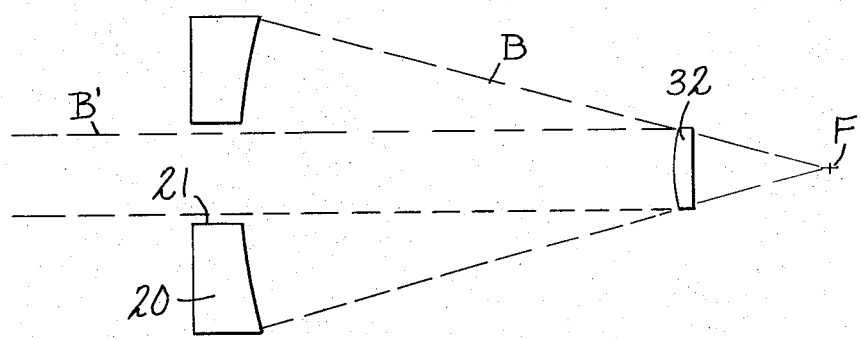
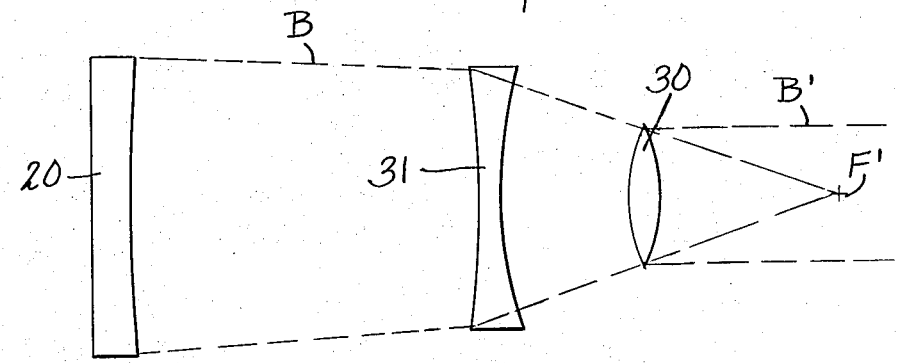
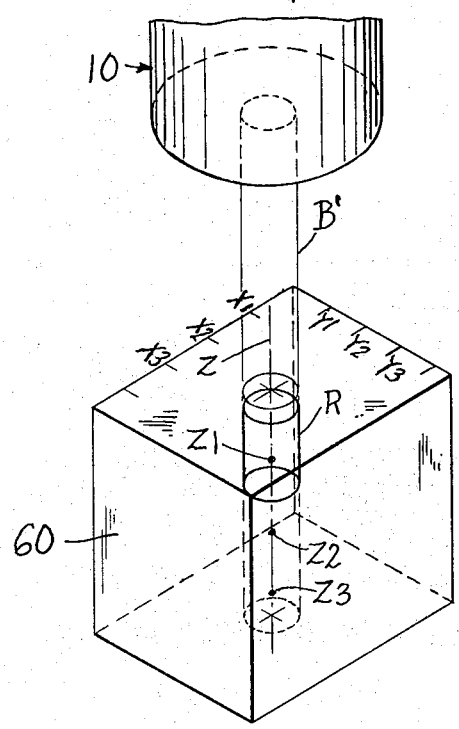
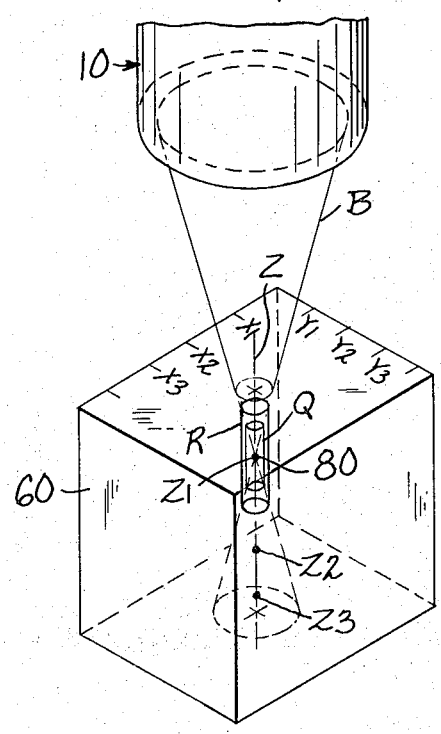

ULTRASONIC TESTING INSTRUMENT AND METHOD

BACKGROUND OF THE INVENTION

This invention relates to an instrument employing an ultrasonic beam and a method employing an ultrasonic beam. More particularly, this invention relates to an instrument and a method for non-destructive and non-invasive testing of an object by means of ultrasonic radiation.

Ultrasonic diagnostic instruments have been widely used in non-destructive testing and have become particularly important in medicine. In general, such ultrasonic instruments operate under either a pulse echo technique or a continuous wave technique. The general principle involves directing an ultrasonic beam at an object to be tested, and monitoring the returned pulses or echoes that result from the ultrasonic beam impinging on boundaries between materials of differing acoustical impedance. By evaluating and quantifying the various characteristics of the received echos, it is possible to determine the location of defects or anomalies, analyze properties of various objects, and by means of Dopper shift analysis, determine the movement or speed of various materials. Ultrasonic instruments are particularly applicable in determining the location and size of defects, either in industrial materials, such as metals, plastics, or rubber, or in organic tissue of concern in diagnostic medicine and related fields. Among the physical properties of materials, that may be quantified and identified by means of ultrasonic instruments are velocity, acoustic absorption, acoustic scattering, acoustic impedance, and acoustic reflectivity.

Conventional ultrasonic diagnostic instruments employ a transmitter usually in the form of a curved piezoelectric transducer element that generates an ultrasonic beam. The ultrasonic beam is passed through a liquid path to the object to be tested. In some instances the object to be tested is placed directly near the source of the ultrasonic beam. In order to obtain sufficient echo response and desirable resolution, it is necessary that the beam be of sufficient intensity. The requisite intensity is obtained by focusing the ultrasonic beam in the immediate vicinity of the test region.

The means for focusing may be provided by the curvature of the transducer element itself in which case the focal point will be approximately the center of curvature of the transducer. The focusing may also be provided by means of a lens or reflector, or combination of such elements. In summary, conventional ultrasonic instruments require that the focal point of the ultrasonic beam be established in the immediate vicinity of the test region, within the object to be tested and all such instruments employ means to focus the ultrasonic beam.

Limitations of the use of conventional focused ultrasonic analysis can be understood by consideration of two characteristics of focus type systems—the necessity of obtaining multiple focal points and the non-uniform response from regions remote from the focal point.

That the region to be tested is confined to the immediate vicinity of the focal point presents a number of limitations in conventional ultrasonic testing methods. Properties of the object tested will be analyzed with highest resolution and with the highest degree of accuracy within the immediate vicinity of the focal point where the energy intensity is highest and the beam width narrowest. However, in practice, data from positions away from the focal point are normally incorporated into the final analysis even though resolution and accuracy are increasingly lessened the more remote the position from the focal point.

Conceptually a region to be tested may be viewed as a three dimensional grid system defined by axes x, y, and z, axes x and y defining a horizontal plane, and axis z denoting a vertical component or depth within the object. For a given depth z it can be seen that the area defined by an xy plane can be tested by orderly positioning the testing instrument at successive coordinates in the xy-plane and processing the received echoes. The focal point of the ultrasonic beam will thus be positioned at a depth z within the object.

It is apparent that if each depth is to be examined under optimal conditions, the focal point of the ultrasonic beam must be repositioned at the new depth. A more detailed and accurate test will be a function of a larger number of discrete focal points and smaller incremental distances of repositioning the focal point along the line z within the object to be tested. As previously discussed, there may be responses received from points away from the focal point and therefore in practice useful data can be received from within a depth interval surrounding a given depth z. For purposes of discussion the useful length of an ultrasonic beam may be referred to as the depth of field or investigative interval. If another region to be tested is beyond the investigative interval, the beam must be refocused to the new region.

A number of inventions have attempted to deal with the depth of field problem and the requirements that the ultrasonic beam be refocused or a new focus established when a new test region is to be analyzed. One technique for dealing with the problem is to place a lens into the beam and mechanically shift the lens to establish a new focus. Another method is to use multiple electrodes on the transducer and by electrical means shift the focal point of the beam.

SUMMARY OF THE INVENTION

This invention provides an ultrasonic testing instrument which employs a narrow collimated beam of ultrasonic energy. The system for producing the collimated beam may take a variety of forms. One embodiment employs a piezoelectric transducer which generates a converging beam of ultrasonic energy. The generated beam is interrupted by a diverging acoustical lens positioned between the transducer and the focal point of the generated beam. The acoustical diverging lens is designed and positioned in such a manner that a collimated beam is produced. The collimated beam is of sufficient intensity to produce useful testing data upon placing an object to be tested at the beam exit of the ultrasonic instrument. Other embodiments of the testing instrument employ a diverging acoustical reflector to produce a collimated beam and/or a system of diverging and converging lenses and/or reflectors.

By virtue of the collimated ultrasonic beam, the invention also provides for a new and improved method of non-destructive and non-invasive testing of objects along a line of depth by directing a high intensity collimated beam along a line of depth to be tested and receiving and processing responses indicative of the acoustical impedance at boundaries of regions of different acoustical impedance. This latter method is accomplished without the necessity of producing multiple focal points of the ultrasonic beam along the line of depth. The invention also encompasses a method for irradiating tissue by directing a collimated beam of high intensity ultrasonic energy at the tissue to be irradiated.

OBJECTS OF THE INVENTION

An object of this invention is to provide a new and improved ultrasonic testing instrument employing an ultrasonic beam having a very large depth of field or investigative interval.

An object of this invention is to provide a new and improved ultrasonic testing instrument which can test along a line of depth of an object with a substantially uniform degree of resolution.

An object of this invention is to provide a new and improved ultrasonic testing instrument which can test along a line of depth of an object without the necessity of providing for a plurality of ultrasonic beam focal points.

An object of this invention is to provide a new and improved ultrasonic testing instrument employing a substantially collimated ultrasonic beam.

An object of this invention is to provide a new and improved ultrasonic testing instrument which provides for a high intensity ultrasonic beam.

An object of this invention is to provide a new and improved ultrasonic testing instrument which increases the intensity of a generated ultrasonic beam by means of producing a narrow collimated beam.

An object of this invention is to provide for a new and improved ultrasonic testing instrument with a substantially increased depth of field or investigative interval without requiring an increase in the energy output of the ultrasonic transmitter.

An object of this invention is to provide for a new and improved method for the non-destructive and non-invasive testing of materials by means of a high intensity collimated ultrasonic beam.

An object of this invention is to provide for a new and improved method of irradiation of material by means of a high intensity collimated ultrasonic beam.

Other objects of the invention will become apparent by reference to the detailed description and accompanying drawings.

BRIEF DESCRIPTION OF THE DRAWINGS

FIG. 1 is a side sectional view of the ultrasonic testing instrument, an object to be tested being schematically represented.

FIG. 2 is a side sectional view of an alternate embodiment of the invention.

FIG. 3 is a beam diagram schematically representing a beam system employed in the instrument shown in FIG. 1.

FIG. 4 is a beam system schematically representing a second embodiment of a beam system employed in the instrument of FIG. 1.

FIG. 5 is a beam diagram schematically illustrating a beam system employed in the instrument of FIG. 2.

FIG. 6 is a beam diagram schematically representing an alternate beam system.

FIG. 7 is a schematic view illustrating a collimated ultrasonic beam directed through a three dimensional object to be tested.

FIG. 8 is a schematic view illustrating an ultrasonic beam focused with an object to be tested.

DETAILED DESCRIPTION

Figure 9:
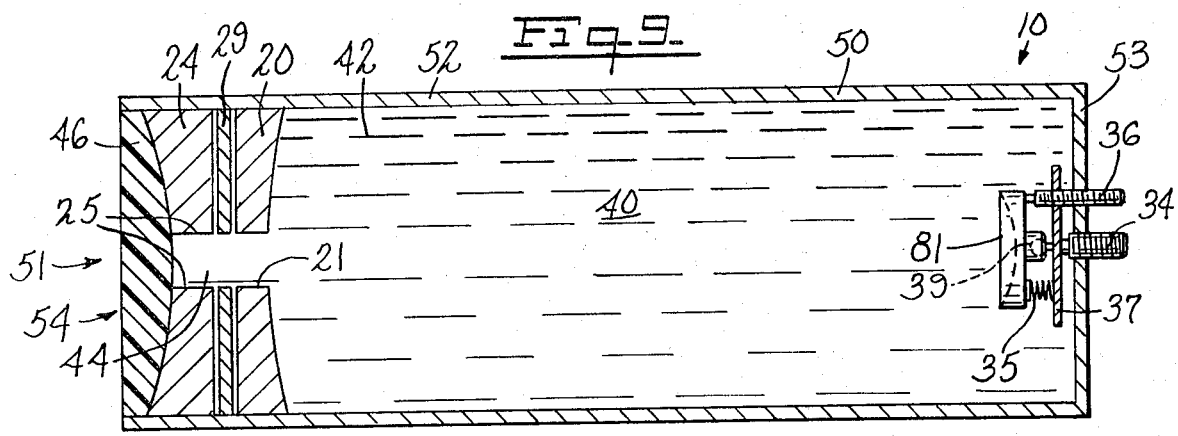
FIG. 9 is a side sectional view of an alternative embodiment of the invention.

An ultrasonic testing instrument shown generally as 10 is illustrated in FIG. 1. Housing 50 having ends 51 and 53 is generally of a substantially cylindrical shape. A transmitter 20 which may be in the form of a curved ceramic piezoelectric transducer is positioned near end 51 within housing 50. Beam exit 54 is centrally positioned in end 53. Excepting the areas in vicinity of exit 54, housing 50 is lined with a sound deadening liner 52.

A central cavity 40 communicates with passage 44. Cavity 40 and passage 44 are filled with a medium, indicated generally as 42, of low sound attenuation which may be in the form of a liquid such as water or a semi-solid material such as agar or plastic. Positioned within central cavity 40 is a diverging acoustical lens 30.

Receiver 24 is positioned proximate the beam exit 54 and is of a generally annular type configuration having a receiver bore 25 which defines passage 44 leading to exit 54. Membrane 46 adjacent to receiver 24 substantially defines end 53. Membrane 46 which may be constructed of polyurethane forms a surface of contact for the object to be tested shown generally as 60.

Transmitter 20, receiver 24 and lens 30 are symmetrically positioned on a central axis extending through beam exit 54. Testing instrument 10 may employ ultrasonic transmitter 20 and ultrasonic receiver 24 which are of conventional form and capability. Transmitter 20 may be in the form of a ceramic piezoelectric transducer constructed of lead zirconate titanate (PZT). Specific forms and specifications of transmitter 20 will be detailed below. Transmitter 20 may communicate electrically with an activator means which activates an ultrasonic pulse, or a gated continuous wave of a given frequency, or a gated frequency modulated wave for a specific time interval in transmitter 20.

Receiver 24 may also be in the form of a piezoelectric transducer. Receiver 24 is generally capable of receiving ultrasonic pulses which are reflected from surfaces at the boundaries of regions of differing acoustical impedance within the object to be tested. Receiver 24 is in electrical communication with a processing and signal means (not shown). The combination of receiver 24 and processing and signal means may take a wide variety of forms which are well known in the ultrasonic instrument arts. In general, the latter components are capable of receiving an echo indicating the frequency and magnitude of the echo response, and in connection with a time delay mechanism are capable of generating a signal indicative of the location and magnitude of the acoustical impedance of the tested boundary. In addition, the receiving means may be in electrical communication with the transmitter so that the frequencies of the transmitted beam and the received echo may be compared and frequency shifts detected and signalled.

It should be noted that the generated ultrasonic beam is hereafter denoted by the letter B except for the collimated portion of said beam produced by the collimating means which will be denoted by B'. The acoustical lenses employed in the invention may be constructed from lucite, epoxy cement, or a material of ultrasonic velocity properties different from the surrounding material so that ultrasonic refraction may occur. The lenses are of a form analogous to lens forms in conventional optical lens systems. The lenses may also be constructed from a material with a gradient of changing acoustic velocity resulting in an effective converging or diverging lens property The acoustical lens should also possess low ultrasonic attenuation characteristics. Various design features of lens 30 as well as position characteristics with respect to transmitter and receiver will be described later in this specification. Of additional note is the fact that an ideal ultrasonic collimated beam cannot be produced, but only approximated in practice. All reference hereafter to "collimated" will be interpreted to mean substantially collimated. Some of the specific design considerations detailed herein are based on wave and ray concepts well known from the field of optics which are generally applicable to ultrasonic applications. Lastly, it will be assumed that the surfaces of all lenses, reflectors, and curved transmitters are spherical because of ease of manufacture. Non-spherical designs may lead to improved focusing but are not normally used because of the increased cost of manufacture.

The spatial relationship between transmitter 20 and lens 30 in a preferred configuration is illustrated in FIG. 3. Transmitter 20 which may be a ceramic piezoelectric element of substantially plano-concave form has a focal point F which is located proximate the center of curvature of element 20. Lens 30 is centrally positioned on the central axis A between the transmitter 20 and the focal point F. Collimated beam B' is produced by the passing of the ultrasonic beam B generated by the transmitter at 20 through diverging acoustical lens 30. In order to obtain a collimated beam of sufficient intensity, it is necessary that the diameter of the collimated beam be relatively narrow. Applicable design constraints dictate that lens 30 be positioned relatively close to the focal point if the beam of narrow diameter is to be obtained. The dimensional relationships for an example will be more specifically detailed later in the specification.

With reference to FIG. 4, a converging lens 31 may be positioned on central axis A beyond focal point F so as to produce a collimated beam B'. Again, the requirement for a beam of relatively small diameter dictates that lens 31 be positioned relatively close to focal point F.

An alternate form of the invention is shown in FIG. 2. Transmitter 20 generates an ultrasonic beam B which is directed to acoustical reflector 32 which redirects the beam toward beam exit 54. In this embodiment exit 54 is positioned proximate end 51. Reflector 32 is positioned near end 53 and is suitably designed to produce a substantially collimated beam passing through exit 54. Reflector 32 is a diverging reflector which may be constructed of stainless steel or any other material having a large acoustic impedance relative to the acoustic impedance in the surrounding mediums. Reflector 32 is pivotally mounted on platform 37 which is threadably secured to the end of housing 50 by means of a threaded position adjustment element 34. Brackets 35 and 36 further cooperate to provide an angle adjustment of the reflector about pivot point 39 of platform 37.

As illustrated in the instrument of FIG. 2, transmitter 20 and receiver 24 are in close proximity and are separated by sound insulating material 29 to prevent spurious ultrasonic responses being received by the receiver. The collimated beam B' is produced in region 40 and transmitted through collimated passage 44 defined by central bores 21 and 25 in transmitter 20 and receiver 24 respectively. Cavity 40 and passage 40 are filled with a low sound attenuation medium shown generally as 42, as previously described.

The ultrasonic beam system of the instrument shown in FIG. 2 is further illustrated in FIG. 5. FIG. 5 shows converging transmitter 20 having a focal point F. The diverging reflector which is placed between transmitter 20 and focal point F reflects the ultrasonic wave through bore 21. The design of the reflector including the radius of curvature of the surface and the position of the reflector relatively close to F cooperate to produce the narrow collimated beam B'.

The ultrasonic transmitter 20 may be of a flat disc form so that a substantially collimated ultrasonic beam is initially generated. In such a case the collimated means may comprise a mutliplicity of acoustical lenses arranged to produce a collimated beam of substantially less diameter but greatly increased intensity relative to the original collimated beam. A beam diagram employing such a transmitter is schematically illustrated in FIG. 6. As shown in FIG. 6, transmitter 20 generates a collimated beam which is directed through lens 31. Lens 31 is a converging acoustical lens having a focal point F'. A diverging lens 30 centrally—positioned between lens 31 and focal point F' of lens 31 produces a collimated beam B'. Applicant's invention may employ systems capable of producing a high intensity narrow collimated beam by means of a multiplicity of lenses and/or reflectors.

Applicant's invention may also incorporate a transmitter which includes means for varying the focal length of the generated ultrasonic beam in which case the lenses and/or reflectors would have a mechanism for position adjustment as illustrated by elements 34, 35, 36, 37 and 39 of FIG. 2. The position adjustment would allow for changing the distance between the transmitter and lenses and/or reflectors.

In another embodiment similar to that shown in FIG. 4, converging lens 31 may be replaced by a converging reflector located at the same position beyond focal point F in the same manner as diverging lens 30 in FIG. 3 may be replaced by diverging reflector 32 in FIG. 5. In such a case, transmitter 20 in FIG. 4 should be replaced by the design of transmitter 20 shown in FIG. 5, having a bore 21 to pass the collimated beam B' after reflection from the converging reflector. Alternatively converging lens 31 may be replaced with a series of lenses or reflectors having an identical net converging acoustic property.

The converging element 31 shown in FIG. 4 may optionally be provided with a means for adjusting its position relative to transducer 20 by means of the mechanism shown as elements 34, 35, 36, 37 and 39 in FIG. 2 to assist in obtaining a collimated beam output.

Converging transducer 20 shown in FIG. 4 may be replaced with a planar transducer and a converging element to produce a converging beam identical to that produced by the converging transducer 20. FIG. 6 shows a planar transducer 20 and converging element 31 suitable to produce the necessary converging beam. The converging element 31 may be a lens as is shown in FIG. 6, or a converging reflector.

An example of a design suitable for ultrasonic testing instruments can be obtained by further reference to FIG. 3 and well known formulas. Transmitter 20 has a focal length of $f_a$. The focal point of transducer 20 given by F may be viewed as theoretically equivalent to the focal point of a lens 20 having a semi-aperture of L. It is assumed that the intervening material has low ultrasonic attenuation characteristics. Diverging lens 30 having a focal length $f_b$ is introduced into the ultrasonic beam path at distance d from transmitter 20.

For purposes of developing suitable design parameters, the semi-beam width w at lens 30 of the converging beam from transmitter 20 is l. This can be shown from well known formulas to be $$l = L \frac{(f_a - d)}{f_a}$$

The effective semi-aperture can be controlled by variations in d.

The overall focal length f of the combination of two lenses separated by a distance d and hence transmitter 20 and lens 30 can be given by the formula:

$$\frac{1}{f} = \frac{1}{f_a} + \frac{1}{f_b} - \frac{d}{f_a \times f_b}$$

If beam B' leaving lens 30 is a collimated beam, i.e. focused at infinity, the focal length of lens 30 is given by $$\frac{1}{f_b} = -\frac{1}{f_a \frac{l}{L}}$$

This equation shows that lens 30 is a divergent lens of focal length $f_a \times l/L$. Beam B' leaving lens 30 will be collimated and focused at infinity.

A common frequency employed in ultrasonic testing instruments used in medical applications is 3.5 megahertz generated by a transducer of a 20 mm diameter with a focal length of 10 cm. The transducer therefore has a semi-aperture length of 10 mm. If the collimated output beam is to be 2 mm, the half aperature of the beam at the diverging lens would be one millimeter. Therefore the focal length of a diverging reflector or lens would be given by $$\frac{1}{f_b} = -\frac{1}{f_a \frac{(l)}{L}} \text{ or } f_b \text{ would equal negative } 10 \times \frac{1}{10} \text{ or}$$

negative 1 centimeter. The focal length of the diverging reflector or lens would then be 1 centimeter. The separation distance between the converging transducer and the diverging reflector or lens would be $$d = f_a\left(1 - \frac{l}{L}\right) \text{ or 9 centimeters.}$$

In diagnostic medicine, beam width in the immediate vicinity of the focal point of the transducer approaches 1 mm. However, due to the limited depth of field normally present, the beam diameter grows to 4 mm within 2 cm of the focal point. Using the collimated beam method described in this patent, the 2 mm beam diameter can be maintained over large beam lengths.

Of considerable concern in the use of an ultrasonic testing instrument is the intensity of the collimated beam. It must be of such a magnitude as to get acceptable results at great depths from the transducer. Assuming an optimum energy output per unit area of the transmitter surface, the larger the transducer area, the greater the total energy output. However, as now used, the transducer area plays a key role, not only in the output intensity but in the resulting beam pattern generated as well. For flat transducers, the larger the transducer surface, the more remote the start of the far field (where analyses are normally conducted). For focused transducers, the larger the transducer surface, the smaller and more intense the beam at the focus can be, but the shorter the depth of field. This results in a difficult and unsatisfactory trade off. With the collimated beam generating system, as described in this patent, the final beam shape is determined by the combination of the transducer shape and size and, in addition, by the compensating lens or reflector. A larger transducer area makes possible a greater beam intensity within a collimated beam pattern whose final shape is controlled by the design of the second lens or reflector. The intensity increase is inversely proportional to the squares of the areas of the transducer and the output collimated beam. The theoretical limit of the diameter of the beam is the wavelength of sound constituting the beam. In summary, the collimated beam allows for a high intensity in a narrow beam with large depth of field allowing a large investigation interval with improved resolution.

In operation the object to be tested, 60, is positioned at the exit 54, in contact with membrane 46. Transmitter 20 is energized by electrical activation means and the collimated beam B' exits through opening 54 into object 60 as illustrated in FIG. 7. Note that collimated beam B' may be used to analyze object 60 along the entire length of line Z as shown in FIG. 7. As the ultrasonic beam passes through object 60, the beam may be partially reflected upon encountering boundaries between surfaces of differing acoustical impedance. The rebounded energy or echoes will be received by receiver 24. Information relating to the frequency, number, intensity, etc. of the echoes is received by the receiver 24 and processed in the processing and signal means. Such information may be displayed on a screen or numerically processed. Note fine collimated beam entering 60 in FIG. 7 while a converging-diverging beam exists for FIG. 8. In both FIG. 7 and FIG. 8, the beam systems are separated from object 60 under test for illustration. This space must be a sound conducting system such as water or gel, or it may be absent in a contact test system with the transducer touching the object.

This invention is not limited to embodiments wherein receiver 24 is substantially coaxial with the transmitted ultrasonic beam or transducer as illustrated in FIG. 1 and FIG. 2. This invention encompasses systems such as "pitch-catch" where the receiver is aimed at selective regions in the insonified region and the receiver is not coaxial with the transducer.

FIG. 7 illustrates a collimated beam B' passing from testing instrument 10. Discrete depth coordinates, along line of depth Z are represented by $z_1, z_2, z_3 \ldots$, and planar coordinates determined by the x and y axes are represented by $x_1, x_2, x_3 \ldots$, and $y_1, y_2, y_3 \ldots$, respectively. Test region R is in the vicinity of three dimensional coordinate point ($x_1$, $y_1$, $z_1$.) One method in widespread use in non-destructive testing is to blank out responses received from echoes returned from depths out of the test region and only signals from echoes received from reflectances within a test interval such as R will be received and processed. This blanking out process can be carried out by conventional techniques such as time delay relays which operate on principles based on data ascertained from the time differentials for a beam to travel and rebound from differing of sample test materials. It should be noted that in the region of analysis R in FIG. 7 along depth line Z, the quality of received response will be transmitted in a substantially uniform manner regardless of whether the reflectance location is at the top or bottom or near the middle of region R. It is therefore possible to scan along the entire depth line z, i.e. at coordinate points ($x_1$, $y_1$, $z_2$) ($x_1$, $y_1$, $z_3$) etc. merely by means of appropriately blanking out responses transmitter from regions outside the test region and without the necessity of multiple focusing. It is noted that the successive x and y coordinate changes can be obtained by conventional mechanical and electronic scanning systems which move instrument 10 relative to object 60.

By contrast as illustrated in FIG. 8, conventional ultrasonic testing instruments blanking out responses outside test region R, nevertheless receive responses from region R which are non-uniform due to the depth of field problem. Any response received from a point that is away from focal point 80 will necessarily have a lesser degree of resolution and accuracy than one received from focal point 80. The useful investigative interval shown as Q depends on the f-number of the specific focusing system and the requirements of the analysis. Investigative interval Q may be substantially smaller than Region R. In order to fully scan along depth line z as illustrated in FIG. 8, it would be necessary to move the focal point 80 to depths $z_2$, $z_3$ . . . , as the regions of response below region R, for instance, would conceivably be beyond the depth of field or investigative interval of the ultrasonic beam.

It can thus be seen that the method which is the subject of Applicant's invention is a significant advancement with respect to testing and scanning along a line of depth or any testing requiring a plurality of depth variations in an object to be tested by virtue of the fact that the elaborate apparatus required to obtain successive focal points is eliminated and by virtue of the fact that the response is substantially uniform.

Figure 10:
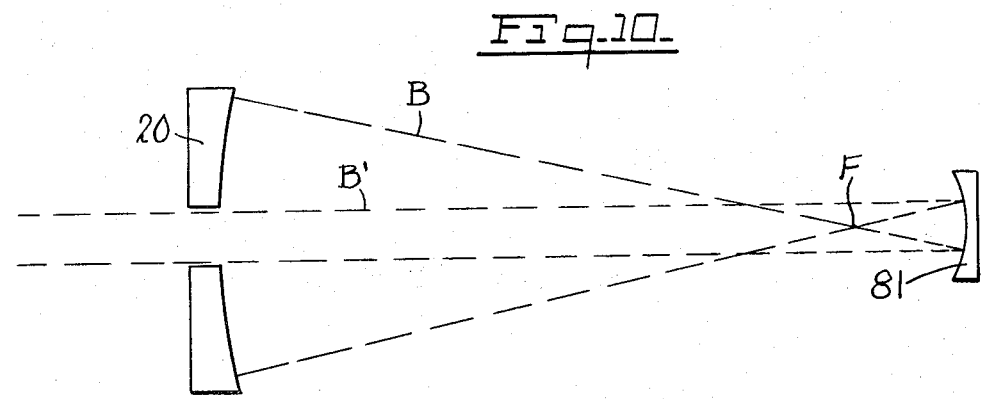
FIG. 10 is a beam diagram schematically representing the beam system employed in the instrument shown in FIG. 9.

FIG. 9 illustrates an alternative embodiment of the invention wherein the beam system illustrated in FIG. 10 is employed. Elements 34, 35, 36, 37 and 39 are used for adjusting the distance between the ultrasonic transducer 20 and the concave reflector 81 in the same manner as described with respect to FIG. 2. The embodiment shown in FIG. 9 differs from the embodiment shown in FIG. 2 in that a concave reflector 81 is used rather than the convex reflector 32 used in FIG. 2.

Figure 11:
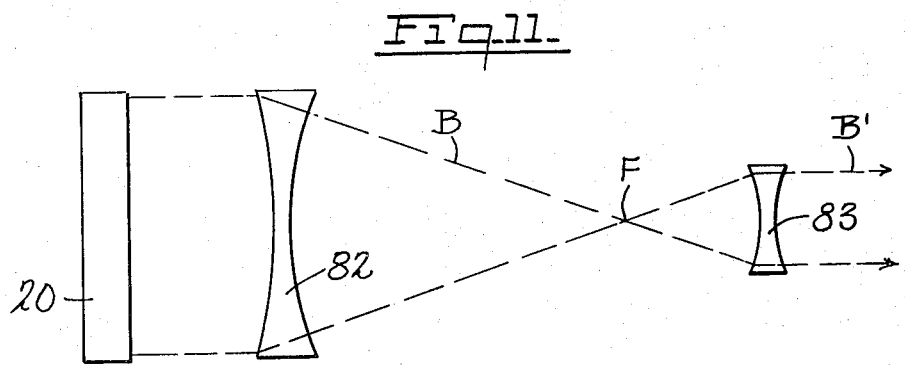
FIG. 11 is a beam diagram schematically representing an alternate beam system.

Referring to FIG. 11, flat disc ultrasonic transmitter 20 generates a wide collimated beam which passes through converging lens 82 thereby generating a converging beam B. After the converging beam B passes through the focal point F, a narrow collimated beam B' is formed by converging lens 83.

Figure 12:
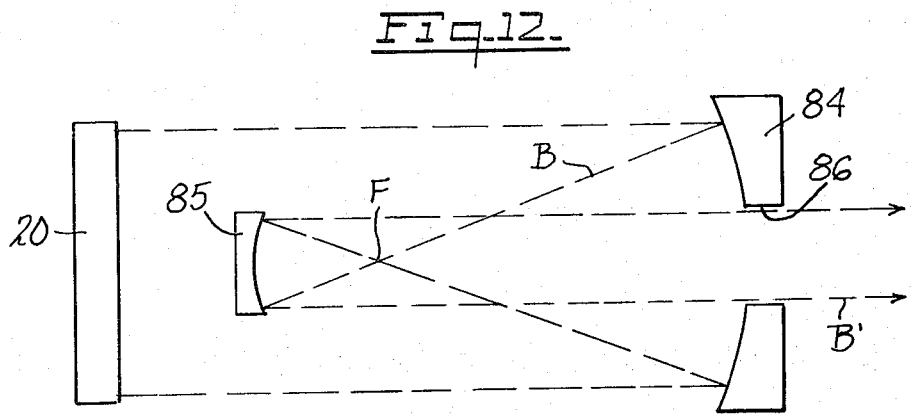
FIG. 12 is a beam diagram schematically representing an alternate beam system.

FIG. 12 shows an alternative beam diagram wherein the flat disc ultrasonic transducer 20 generates a wide collimated beam which is brought to a focus F by a concave reflector 84. Ultrasonic reflector 85 then forms a narrow collimated beam B' which exits through a central bore 86 in reflector 84.

Figure 13:
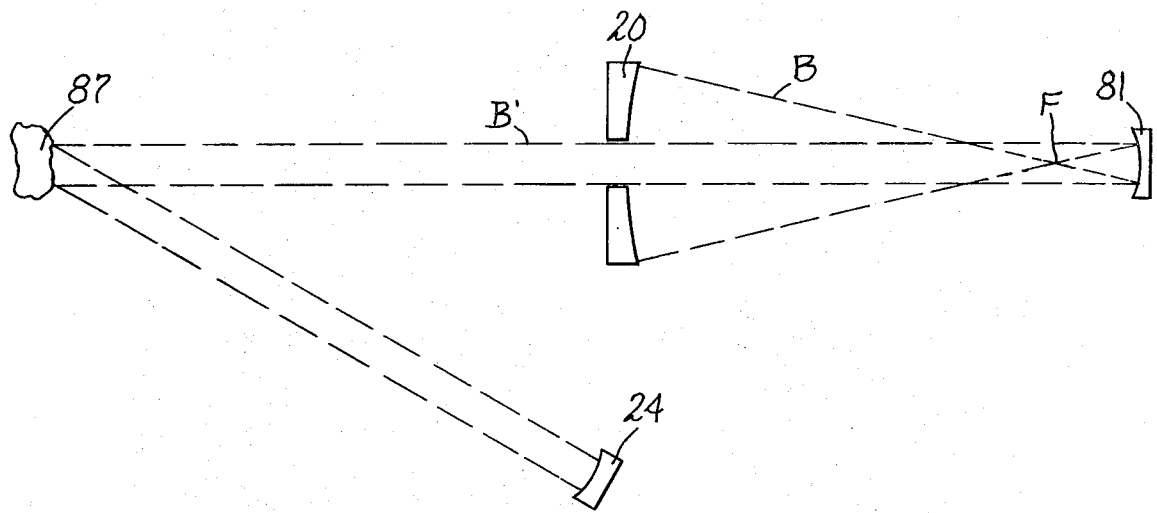
FIG. 13 is a beam diagram showing a receiver transducer which is remotely positioned from a transmit transducer.

FIG. 13 shows a beam diagram wherein the line between the ultrasonic transducer 20 and the test region of interest 87 is not collinear with the line between the ultrasonic receiver transducer 24 and the rest region of interest 87. In this arrangement the ultrasonic receiver transducer 24 is not mounted within the same housing as the transmit transducer 20 as is the case in the embodiment shown in FIG. 9.

Figure 14:
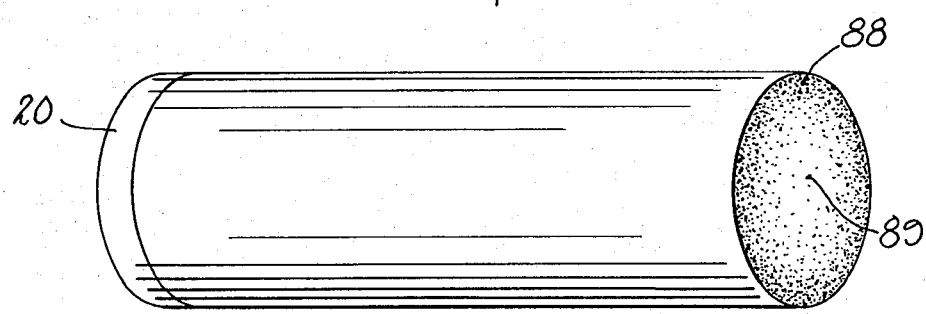
FIG. 14 is a side perspective view of a planar transducer mounted to a material with a gradient of changing acoustic velocity resulting in an effective converging lens property.

FIG. 14 shows a flat disc transmit transducer 20 mounted on a material having a gradient of changing acoustic velocity, wherein the acoustic velocity is greater near the perimeter 88 of the material thereby resulting in an effective converging lens property whereby a converging beam is produced. The elements shown in FIG. 14 may be used instead of the flat disc transducer 20 and conventional converging lens 82 shown in FIG. 11 to produce the converging beam B.

Applicant's invention could also be used as a method to irradiate tumors or other similar material in tissue by means of directing the collimated beam at the tissue to be irradiated. Combinations of several such ultrasonic units could be used as energy sources or a single beam could be oscillated around a remote center to generate sufficiently high energy.

It should also be noted that the ultrasonic testing instrument can be constructed so that it can be hand-held and moved over material to be tested. It can be oscillated by hand or motor driven and it can be placed in a bath driven by a program motor along one or more axes, or several units can be used in combination or in parallel to speed up analysis.

As shown by the various examples and embodiments, various instruments and methods may be made and practiced within the scope of the invention. Accordingly, the appended claims are intended to cover all modifications of the disclosed embodiments as well as other embodiments thereof which do not depart from the spirit and scope of the invention.

I claim:

1. An ultrasonic instrument for use in the non-destructive and non-invasive testing of an object comprising:
   transmitter means for generating a converging beam of ultrasonic energy;
   housing means enclosing said transmitter means and having an exit opening for said beam;
   a medium of low sound attenuation disposed in said housing means, said medium defining the path for the beam of ultrasonic energy from said transmitter means to said exit opening;
   collimating means positioned beyond the focal point of the converging beam to produce a collimated beam passing through said exit opening which remains collimated as the beam passes out of the instrument and into materials of different acoustic indices of refraction; and
   receiver means separate from the transmitter means and responsive to ultrasonic energy returned from an object to be tested by reflection of said collimated beam at boundaries between regions of different ultrasonic transmission characteristics within said object, said receiver means providing an output signal responsive and indicative of said returned energy.

2. The instrument of claim 1 wherein the transmitter means comprises a piezoelectric transducer.

3. The instrument of claim 1 wherein the transmitter means comprises a piezoelectric transducer of a plano-concave shape to generate the converging beam of ultrasonic energy.

4. The instrument of claim 1 wherein said collimating means comprises a converging lens positioned beyond the focal point of said converging beam.

5. The instrument of claim 4 wherein the lens is made of a material of low acoustic attenuation.

6. The instrument of claim 1 wherein the collimating means comprises a converging acoustical reflector positioned beyond the focal point of said converging beam.

7. The instrument of claim 6 wherein the reflector is made of a material of large acoustic impedance relative to the impedance of said medium.

8. The instrument of claim 1 wherein said medium is water.

9. The instrument of claim 1 wherein said medium is agar.

10. The instrument of claim 1 wherein the diameter of the collimated beam at the exit opening is small compared to the diameter of the beam at the transmitter.

11. The instrument of claim 1 wherein said collimated beam is a high intensity beam.

12. The instrument of claim 1 wherein said collimating means comprises a plurality of lenses.

13. The instrument of claim 1 wherein the collimating means comprises a material with a gradient of changing acoustic velocity resulting in an effective converging or diverging lens property.

14. The instrument of claim 1 wherein said collimating means comprises a plurality of reflectors.

15. The instrument of claim 1 wherein said collimating means further comprise means for adjusting the distance between said transmitter means and said collimating means.

16. The instrument of claim 1 wherein the transmitter means comprises a planar piezoelectric transducer to produce a collimated beam, and a converging means for converging the beam.

17. The instrument of claim 16 wherein the converging means is a converging acoustical lens.

18. The instrument of claim 17 wherein the converging means is a converging acoustical reflector.

19. The instrument of claim 17 wherein the converging means comprises a material with a gradient of changing acoustic velocity resulting in effective converging lens property.

20. A method of non-destructive and non-invasive testing along
a line of depth of an object comprising the steps of:
a. generating a converging beam of ultrasonic energy, by means of an ultrasonic transducer;
b. collimating the generated beam after the beam has passed through its focus to form a collimated beam of a higher energy intensity than the energy intensity of the beam upon initial generation which remains collimated as the beam passes into materials of different acoustic indices of refraction;
c. passing the collimated beam along a line of depth within an object to be tested;
d. receiving echoes from the boundaries of regions within the object by means of a second ultrasonic transducer which echoes are characterized by different impedances to the passage of ultrasonic energy; and
e. producing signals indicative of the received echoes.

21. The method of claim 20 further comprising the step of scanning said collimated beam along the surface of the object.

22. The method of claim 20 further comprising passing the beam through a liquid medium.

23. The method of claim 20 wherein the path between the transducer and the object to be tested is not collinear with the path between the object and the second ultrasonic transducer.

24. The method of claim 20 wherein step b further comprises passing said generated beam through a converging lens.

25. The method of claim 20 wherein step b further comprises passing said generated beam through a multiplicity of lenses.

26. The method of claim 20 wherein step d further comprises blanking out said echoes originating outside an interval along a line of depth.

27. The method of claim 26 wherein step d further comprises changing said interval and steps d and e are cyclically repeated.

28. An ultrasonic instrument for use in the non-destructive and non-invasive testing of an object comprising:
a piezoelectric transmitter means for generating a converging beam of ultrasonic energy;
a collimating means located beyond the focal point of the converging beam for generating a collimated beam output which remains collimated as the beam passes out of the instrument and into materials of different acoustic indices of refraction and constructed from a material with a gradient of changing acoustic velocity resulting in an effective converging lens property;
a piezoelectric receiver separate from and independent of the transmitter and responsive to ultrasonic energy returned from the object to be tested by reflection of the collimated beam at boundaries between regions of different ultrasonic transmission characteristics within the object, said receiver providing an output signal responsive and indicative of said returned energy;
a housing enclosing the transmitter means, receiver means, and collimating means, having an exit opening for the collimated beam; and
a medium of low sound attenuation disposed in the housing for providing a path for the ultrasonic sound from the transmitter to the exit opening.

* * * * *

UNITED STATES PATENT AND TRADEMARK OFFICE
CERTIFICATE OF CORRECTION

PATENT NO. : 4,423,637
DATED : January 3, 1984
INVENTOR(S) : Mahlon R. Soloway, M.D.

It is certified that error appears in the above-identified patent and that said Letters Patent is hereby corrected as shown below:

Column 6, line 10, "40" (second occurrence) should be --44--.

Column 10, line 6, "rest" should be --test--.

Signed and Sealed this

First Day of May 1984

[SEAL]

Attest:

GERALD J. MOSSINGHOFF

Attesting Officer     Commissioner of Patents and Trademarks